United States Patent

Cheng et al.

[11] Patent Number: 5,909,476
[45] Date of Patent: Jun. 1, 1999

[54] ITERATIVE PROCESS FOR RECONSTRUCTING CONE-BEAM TOMOGRAPHIC IMAGES

[75] Inventors: Ping-Chin Cheng, Williamsville, N.Y.; Donald L. Snyder, Clayton; Joseph A. O'Sullivan, St. Louis, both of Mo.; Ge Wang, Iowa City, Iowa; Michael W. Vannier, Alton, Ill.

[73] Assignees: University of Iowa Research Foundation, Iowa, Iowa; Washington University, St. Louis, Mo.; Research Foundation of State of NY, Amherst, N.Y.

[21] Appl. No.: 08/935,205

[22] Filed: Sep. 22, 1997

[51] Int. Cl.⁶ .......................................... A61B 6/03
[52] U.S. Cl. .............................. 378/4; 378/901
[58] Field of Search .................. 378/4, 901; 250/363, 250/4

[56] References Cited

U.S. PATENT DOCUMENTS

| | | | |
|---|---|---|---|
| 5,210,421 | 5/1993 | Gullberg et al. | 250/363.04 |
| 5,253,171 | 10/1993 | Hsiao et al. | 378/4 |
| 5,270,926 | 12/1993 | Tam | 378/4 |
| 5,338,936 | 8/1994 | Gullberg et al. | 250/363.04 |
| 5,376,795 | 12/1994 | Hasegawa et al. | 250/363.04 |
| 5,402,460 | 3/1995 | Johnson et al. | 378/10 |
| 5,414,623 | 5/1995 | Lu et al. | 382/131 |
| 5,463,666 | 10/1995 | Eberhard et al. | 378/4 |
| 5,559,335 | 9/1996 | Zeng et al. | 250/363.04 |
| 5,565,684 | 10/1996 | Gullberg et al. | 250/363.04 |

*Primary Examiner*—David Vernon Bruce
*Attorney, Agent, or Firm*—Needle & Rosenberg, P.C.

[57] ABSTRACT

In the present invention, an iterative process is provided for cone-beam tomography (parallel-beam and fan-beam geometries are considered as its special cases), and applied to metal artifact reduction and local reconstruction from truncated data, as well as image noise reduction. In different embodiments, these iterative processes may be based upon the emission computerized tomography (CT) expectation maximization (EM) formula and/or the algebraic reconstruction technique (ART). In one embodiment, generation of a projection mask and computation of a 3D spatially varying relaxation factor are utilized to compensate for beam divergence, data inconsistency and incompleteness.

12 Claims, 12 Drawing Sheets

ITERATIVE PROCESS FOR RECONSTRUCTING CONE-BEAM TOMOGRAPHIC IMAGES

BACKGROUND OF THE INVENTION

1. Field of the Invention

The present invention generally relates to a system and method for reconstructing cone-beam tomographic images and particularly to an iterative process for performing such functionality.

2. Description of the Prior Art

Nondestructive analysis and visualization of three-dimensional microstructures of opaque specimens are important techniques in biomedical and material sciences and engineering. Due to its penetration ability and contrast mechanism, X-ray microtomography is a powerful tool in this type of application. For example, and as described in G. Wang et al., "Cone-beam X-ray microtomography", *Multidimensional microscopy*, Springer-Verlag, New York, Chapter 9, pages 151–169 (1994), an X-ray shadow projection microscope with a microtomography capability is being developed at the State University of New York at Buffalo (SUNY/Buffalo). FIG. 1, described in further detail later, shows such a system.

Cone-beam geometry is also important for emission tomography, medical and industrial X-ray CT. Due to 3D divergency, reconstruction from cone-beam data is much more intricate than in parallel-beam or fan-beam geometry. Having been studied for many years, cone-beam tomography remains a major topic in CT.

A cone-beam reconstruction formula for an infinitely long scanning line has been developed. Additionally, a formula has been derived for reconstruction of a real function with a compact support under the condition that almost every plane through the support meets a scanning locus transversely. A cone-beam reconstruction formula for two intersecting source circles has also been established. Thorough theoretical analyses on cone-beam reconstruction have been reported by Tuy, Smith and Grangeat. As a result, the following sufficient condition for exact cone-beam reconstruction has been developed:

if on every plane through an object there exists at least one source point, exact cone-beam reconstruction can be achieved.

A theoretical framework for local cone-beam reconstruction has been developed. The concept of the planar region of an object as intersection of the object support and a set of planes has been defined, proving that if a source curve is connected and compact, and if its convex hull contains a planar region, the cone-beam data from the source curve is complete for exact reconstruction of the planar region.

An estimation formula for local reconstruction and a convergence condition for the formula have also been created.

Exact cone-beam reconstruction algorithms have been implemented in the past, including filtered backprojection algorithms. Among current exact algorithms, a direct Fourier transform method is computationally the most efficient for a sufficiently large amount of data.

Approximate cone-beam reconstruction algorithms are also important in practice. Generally speaking, approximate cone-beam reconstruction cannot be avoided in the cases of incomplete scanning geometry and partial detection coverage. Furthermore, approximate reconstruction is usually associated with higher computational efficiency, and likely less image noise and ringing. Others have adapted the equispatial fan-beam algorithm for cone-beam reconstruction with a circular scanning locus. Because this algorithm is limited by circular scanning, spherical specimen support and longitudinal image blurring, it has been extended in various ways.

Tam, U.S. Pat. No. 5,270,926, discloses an iterative algorithm for cone-beam reconstruction from incomplete data. In this algorithm, Radon data are first computed, and missing data initialized to zero. Then, an image volume is reconstructed slice-by-slice via 2D filtered backprojection. Projection data are corrected by a priori information on the object support, upper and lower bounds of projection values, and reprojected to calculate the missing data. The steps are repeated until some convergence criterion is satisfied.

However, the convergence and optimality of this iterative algorithm have not been established. Other existing cone-beam algorithms require that projections be complete at least along one direction, and therefore cone-beam reconstruction is impossible in cases where objects contain X-ray opaque components and/or are larger than the cone-beam aperture defined by effective detection area and X-ray source position.

The expectation maximization (EM) approach is well known. This iterative formula has been interpreted in a deterministic sense, and its desirable theoretical properties have been established. Based on this formula, 2-D parallel-beam CT algorithms for metal artifact reduction and local reconstruction from truncated data may be developed.

SUMMARY OF THE INVENTION

In the present invention, an iterative process is provided for cone-beam tomography (parallel-beam and fan-beam geometries are considered as its special cases), and applied to metal artifact reduction and local reconstruction from truncated data, as well as image noise reduction. In different embodiments, these iterative processes may be based upon the emission computerized tomography (CT) expectation maximization (EM) formula and/or the algebraic reconstruction technique (ART). In one embodiment, generation of a projection mask and computation of a 3D spatially varying relaxation factor are utilized to compensate for beam divergence, data inconsistence and incompleteness.

DETAILED DESCRIPTION OF THE INVENTION

Figure 1:
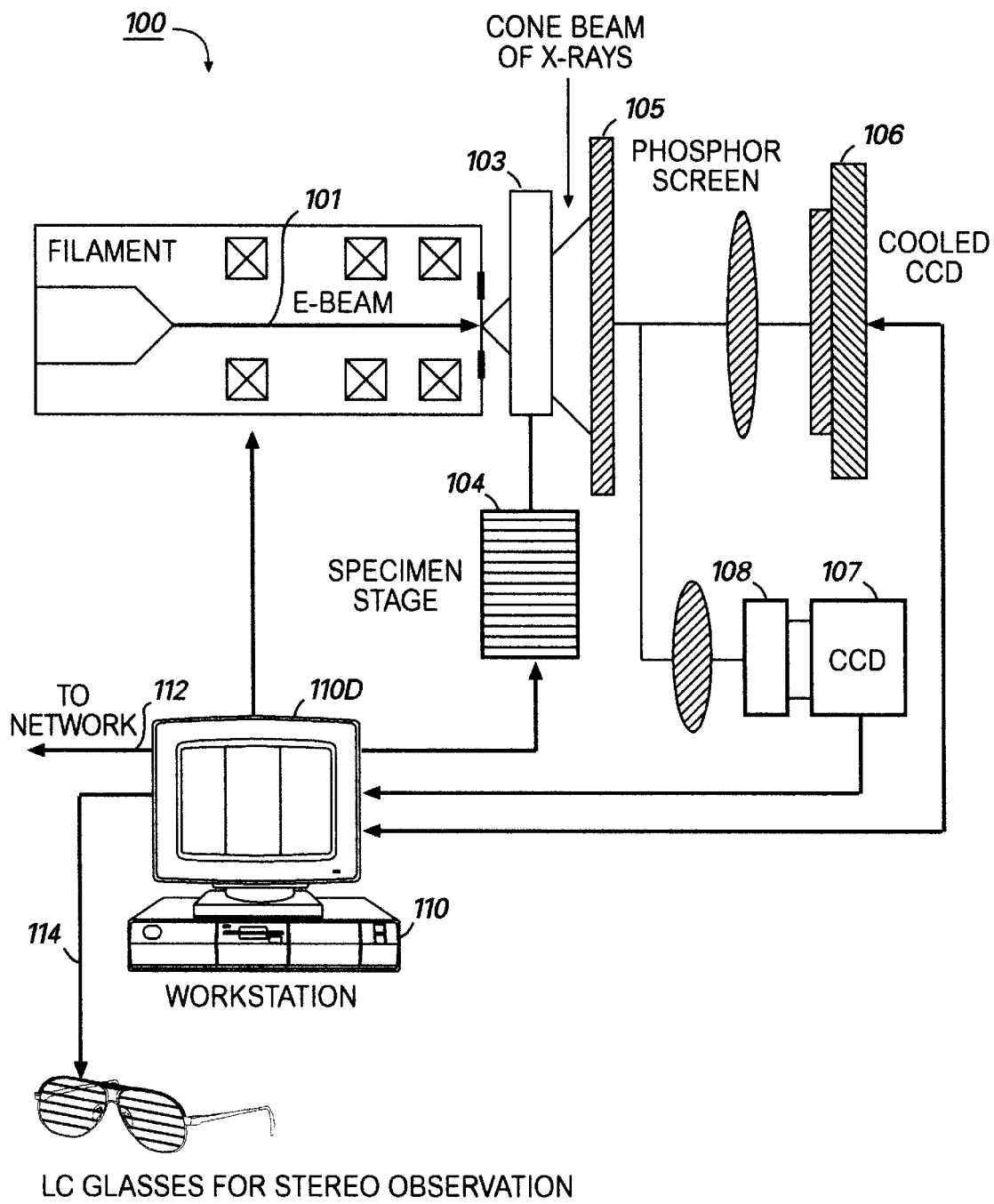
FIG. 1 is a block diagram of the components that may be used to implement the present invention.

In a preferred embodiment, the present invention may be implemented in conjunction with a cone-beam x-ray microtomographic system, such as that shown schematically in FIG. 1.

As illustrated in FIG. 1, the X-ray microtomographic system 100 that may be used in the present invention uses an X-ray point source generated by a microfocused e-beam 101. This point source can be electro-magnetically steered across the target window in a precisely controllable fashion. A specimen 103 is mounted on a mechanical stage 104, which can be translated and/or rotated under control of a programmable control unit. Projection data coming through a phosphor screen 105 can be recorded on a cooled CCD camera 106, transferred into a high-performance computing unit (workstation) 110 and reconstructed for cross-sectional or volumetric images as well as stereo-image pairs. Additionally projection data may pass through an intensifier 108, through a CCD camera 107, and into the computer system 110. The computer system 110 may include a graphical display 110D, and may be connected to other peripheral systems through a network 112, as well as to LC glasses 114, etc. In a preferred embodiment, workstation 110 may comprise a Silicon Graphics $O_2$ computing platform (Silicon Graphics, Inc.; Mountain View, Calif., USA), or any other suitable computing system.

Those having ordinary skill in the art will readily recognize that the system of FIG. 1 is only one example of the type of system that may be used according to the teachings of the present invention. Other examples of X-ray medical imaging systems that may be used with the present invention are the Electron-beam CT scanner developed at the Imatron (described in D. P. Boyd and M. J. Lipton, Cardiac computed tomography, *Proc. IEEE*, Vol. 71, pages 298–307, 1983); the Dynamic Spatial Reconstructor developed at the Mayo Clinic to investigate the heart and lungs (described in Robb, "X-ray Computed Tomography: Advanced Systems in Biomedical Research", *Three Dimensional Biomedical Imaging*, CRC Press, Vol. 1, Chap. 5, pages 107–164 [1985]); the TRIDIMOS project to measure the bone mineral content of lumbar vertebrae (described in Grangeat, "TRIDIMOS: Imagerie 3D de la mineralisation des vertebres lombaires", *CNES-LETI*, No. 853/CNES/89/5849/00, [1989]); the MORPHOMETER project to image vessel trees and bone structures (described in Saint-Felix et al., "3D reconstruction of high contrast objects using a multi-scale detection/estimation scheme", *3D Imaging in Medicine: Algorithms, Systems, Applications* (*NATO ASI Series*), Springer Verlag, Vol. 60, pages 147–158, [1990]); a microtomographic imaging system to study small objects like biopsies (described in Morton et al., "Three-dimensional X-ray microtomography for medical and biological applications", *Phys. Med. Biol.*, Vol. 35, No. 7, pages 805–820, [1990]); and a cone-beam imaging system for angiography (described in Saint-Fmboxelix et al., "In vivo evaluation of a new system for 3D computerized angiography", *Phys. Med. Biol.*, Vol. 39, pages 583–595, [1994]).

The present invention may also be used in conjunction with industrial imaging systems as well. In industrial imaging, cone-beam scanners are used for nondestructive evaluation of products (see, e.g., Feldkamp et al., "Practical cone-beam algorithm", *J. Opt. Soc. Am.*, Vol. 1(A), pages 612–619, [1984] and Vickers et al., "A revolutionary approach to industrial CT using cone-beam reconstruction", *Topical Proceedings of the ASNT: Industrial Computerized Tomography*, pages 39–45, [July, 1989]).

1. The Iterative Debluring Process

The following notation of Equation (1) may be used to define the linear, discrete and non-negative deblurring problem:

$$\sum_{\vec{x} \in X} h(\vec{y} \mid \vec{x}) c(\vec{x}) d\vec{x} = a(\vec{y}) \tag{1}$$

where $a(\vec{y})$ is an observed function, $h(\vec{y} \mid \vec{x})$ is a known blurring kernel, $c(\vec{x})$ is a function to be recovered, $\vec{x} \in X$, $\vec{y} \in Y$ and X and Y are finite dimensional. The following iterative inversion formula of Equation (2) has been proposed:

$$c_{k+1}(\vec{x}) = c_k(\vec{x}) \frac{1}{H(\vec{x})} \sum_{\vec{y} \in Y} h(\vec{y} \mid \vec{x}) \left[ \frac{a(\vec{y})}{\sum_{\vec{x}' \in X} h(\vec{y} \mid \vec{x}') c_k(\vec{x}')} \right] \tag{2}$$

where $$H(\vec{x}) = \sum_{\vec{y} \in Y} h(\vec{y} \mid \vec{x}) \tag{3}$$

$C_k(\vec{X})$ and $C_{k+1}(\vec{X})$ are current and updated guesses of, $c(\vec{x})$, k=0, 1, . . . The following Equation (4) is the I-divergence:

$$I(a \parallel b) = \sum_{\vec{y} \in Y} a(\vec{y}) \log \frac{a(\vec{y})}{b(\vec{y})} - \sum_{\vec{y} \in Y} [a(\vec{y}) - b(\vec{y})] \tag{4}$$

where $a(\vec{y})$ and $b(\vec{y} : c)$ are measured and predicted data:

$$b(\vec{y} : c) = \sum_{\vec{x} \in X} h(\vec{y} \mid \vec{x}) c(\vec{x}) \tag{5}$$

A number of properties have been identified (including I-divergence minimization) under the following assumptions:

1. $a(\vec{y}) \geq 0$ for all $\vec{y}$,

2. $a(\bullet)$ is not always equal to zero,

3. $a(\vec{y})$ is summable,

4. $h(\vec{y}|\vec{x}) > 0$ for all $\vec{x}, \vec{y}$,

5. $h(\vec{y}|\vec{x})$ is summable with respect to $\vec{y}$ for all $\vec{x}$.

However, the requirement for a positive blurring kernel, $h(\vec{y}|\vec{x}) > 0$, is too strong in practice. Non-zero entries of the blurring kernel are sparse in X-ray CT. Therefore, the methodology (described in Donald, Snyder, T. J. Schultz and J. A. O'Sullivan, "Deblurring Subject to Nonnegativity Constraints", *IEEE Trans. Signal Processing*, pp. 1143–1150, May 1992) may be paralleled to demonstrate the validity of established properties of the sequence $\{c_k(\cdot)\}$ under the following extended assumptions:

1. $a(\vec{y}) > 0$ for all $\vec{y}$,

2. $a(\vec{y})$ is summable,

3.
$$H(\vec{x}) = \sum_{\vec{y} \in Y} h(\vec{y}|\vec{x}) > 0,$$

4.
$$H*(\vec{y}) = \sum_{\vec{x} \in X} h(\vec{y}|\vec{x}) > 0,$$

5. $h(\vec{y}|\vec{x}) \geq 0$ for all $\vec{x}, \vec{y}$,

6. $h(\vec{y}|\vec{x})$ is summable with respect to $\vec{x}$ and $\vec{y}$.

Several comments regarding the above extended assumptions are provided below. First, although $a(\vec{y}) > 0$ may appear more restrictive than the original $a(\vec{y}) \geq 0$, it is not. Actually, a deblurring problem with $a(\vec{y}) \geq 0$ can be transformed to the one with $a(\vec{y}) > 0$ by the following pre-conditioning procedure: if $a(\vec{y}_0) = 0$, $c(\vec{x})$ is set to zero for all $\vec{x} \in X(\vec{y}_0)$, where $X(\vec{y}_0) = \{\vec{x} \in X, h(\vec{y}_0|\vec{x}) > 0\}$, then $\vec{y}_0$ and $X(\vec{y}_0)$ can be removed from Y and X, respectively. Also, $H(\vec{x}) > 0$ means that $c(\vec{x})$ is measured at any specific $\vec{x}$. If $H(\vec{x}_0) = 0$, then $c(\vec{x}_0)$ is totally unobservable. Hence, $\vec{x}_0$ can be removed from x. On the other hand $H*(\vec{y}) > 0$ means that every $a(\vec{y})$ carries a certain amount of information about $c(\bullet)$. Actually, if $H(\vec{y}_0) = 0$, $h(\vec{y}_0|\vec{x}) = 0$ for all $\vec{x}$, then no information about $c(\bullet)$ can be derived from $a(\vec{y}_0) \equiv 0$. Therefore, $\vec{y}_0$ can be removed from Y. These pre-conditioning operations exclude uninteresting situations. Actually, the pre-conditioning for $a(\vec{y}) = 0$ can be naturally implemented by setting $$\frac{a(\vec{y})}{\sum_{\vec{x}' \in X} h(\vec{y}|\vec{x}')c_k(\vec{x}')}$$

to one whenever the quotient is "zero over zero". Note that EM-like iterative deblurring could never lead to a quotient of a positive numerator divided by a zero denominator if the initial guess is positive. Setting "zero over zero" to one makes I-divergence well defined even when $a(\vec{y}) = 0$.

It is also known that the above EM formula for emission CT has a geometrical explanation. Ratios between measured and predicted data are used to correct a guess to the underlying function $c(\vec{x})$. If difference is used instead of ratio to quantify discrepency between measured and predicted data, the following additive iterative deblurring Equation (6) can be obtained:

$$c_{k+1}(\vec{x}) = c_k(\vec{x}) + \frac{1}{H(\vec{x})} \sum_{\vec{y} \in Y} h(\vec{y}|\vec{x}) \left[ \frac{a(\vec{y}) - \sum_{\vec{x}' \in X} h(\vec{y}|\vec{x}')c_k(\vec{x}')}{H*(\vec{y})} \right] \quad (6)$$

2. Cone-Beam Iterative Processes

Because X-ray projection can be considered a linear process, iterative reconstruction can be formulated based on two iterative deblurring formulas. Theoretically, every cone-beam datum is a linear integral along an X-ray path. To avoid the singularities in iterative cone-beam reconstruction and to facilitate the development of a suitable process, in the present specification the problem is cast in discrete domains.

Figure 2:
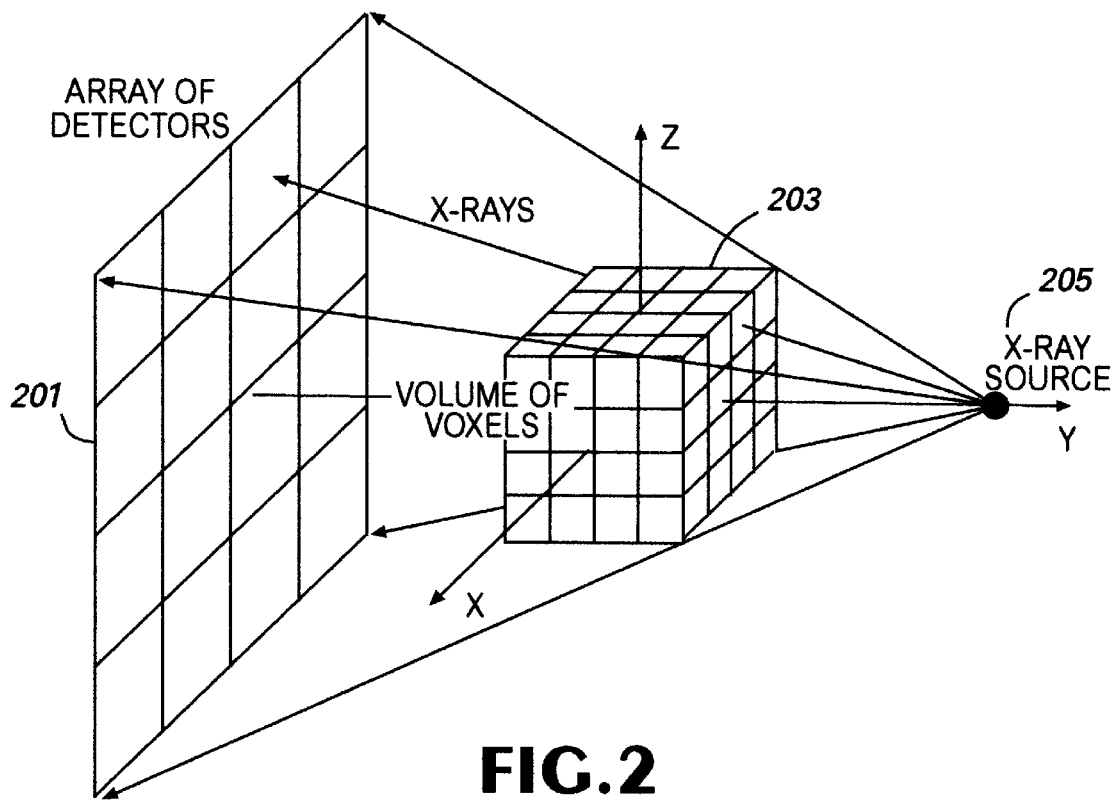
FIG. 2 illustrates a discretized cone-beam imaging geometry.
Figure 3:
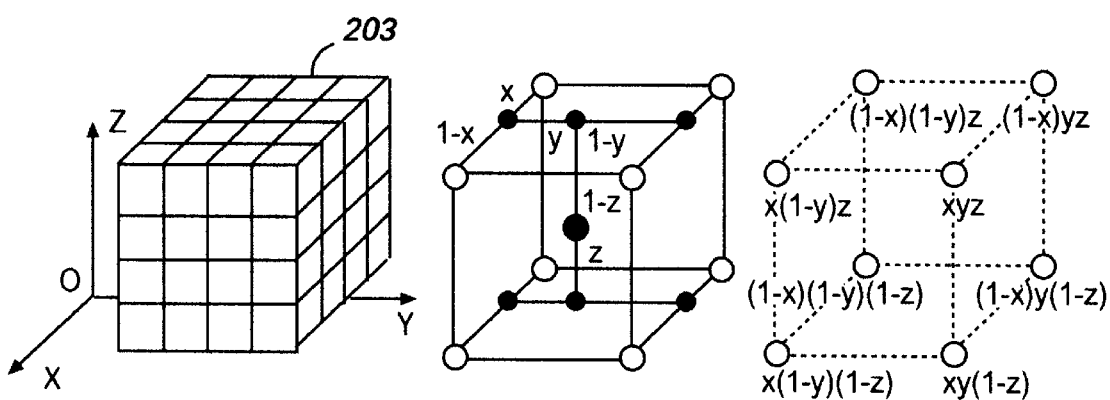
FIG. 3 illustrates the computation of bi-linear interpolation coefficients of the eight neighbors of an arbitrary point in a volumetric image.

After the object and the detection plate has been discretized as shown in FIG. 2, the continuous cone-beam projection measurement can be approximated as a set of values at a 2D detection grid, each of which equals a sum of weighted values of those voxels 203 that are in a neighborhood of the corresponding X-ray 205. Specifically, an X-ray path is divided at equi-distance points, the distance can be, for example, the voxel side length. The value of each dividing point is assumed to be the bi-linear interpolation of the values of its eight nearest voxel neighbors. The interpolation weights are linearly determined in a traditional way, as illustrated in FIG. 3. A projection datum associated with an X-ray path is modeled as the sum of incremental contributions from all the dividing points along the path. Other models are also possible to approximate this process.

Figure 4:
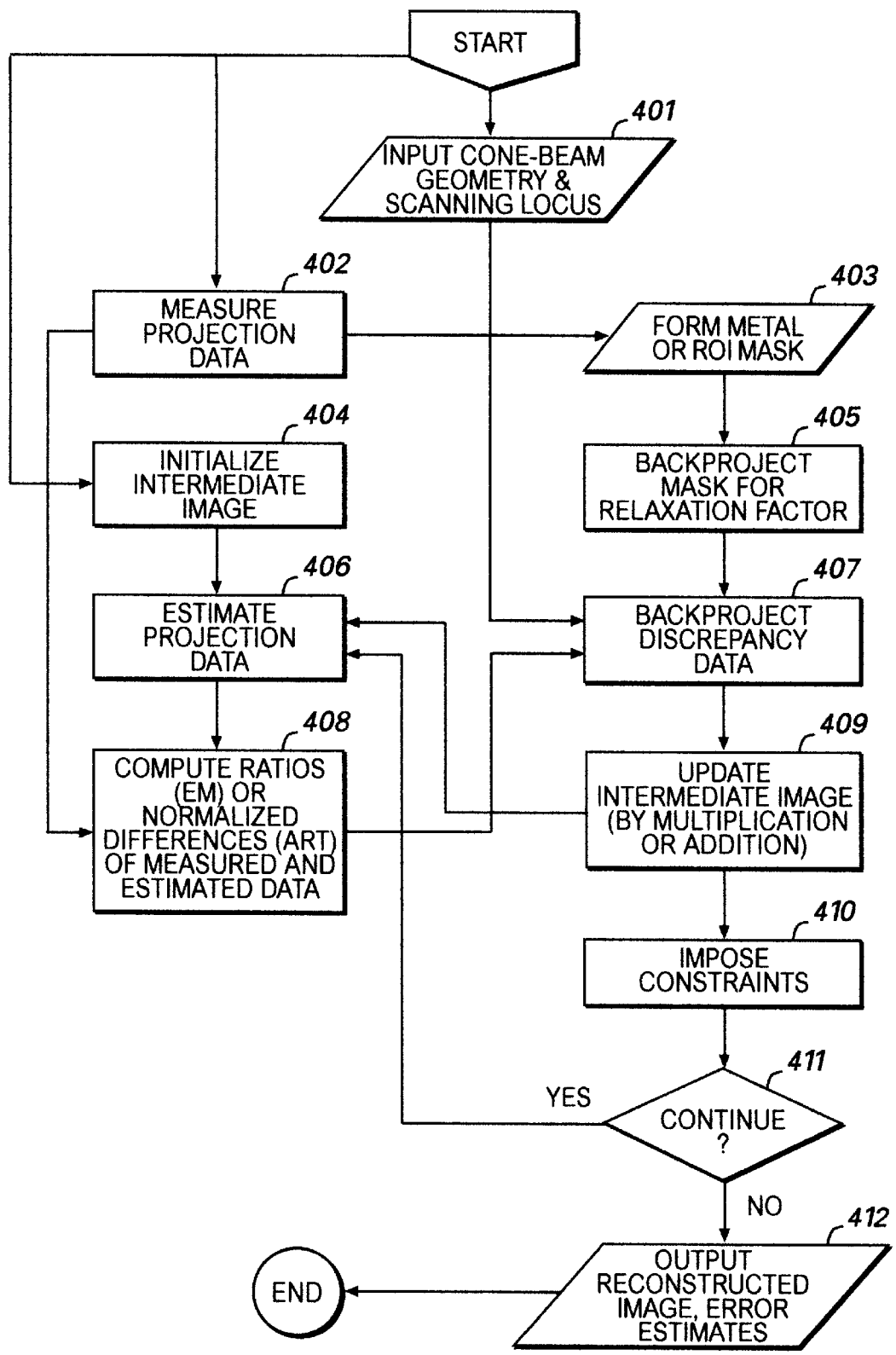
FIG. 4 is a process diagram depicting EM-like and ART-like cone-beam image reconstruction.

FIG. 4 is a flowchart of the iterative cone-beam process of the present invention. Again, in one embodiment, this process may be performed by the processing system 110 of FIG. 1, which in one embodiment may be a Silicon Graphics $O_2$ computing platform, as previously described. The process depicted in FIG. 4 is described in further detail below.

FIG. 4 describes two cone-beam reconstruction processes adapted from the two iterative deblurring formulas, respectively. In step 401, a cone-beam imaging geometry is specified, including the distance between the source and the detection plate, the dimensions of the plate, as well as the distribution of detectors on the plate. Also, measured cone-beam projections are input in step 402.

In step 403, a projection mask is generated from measured cone-beam data, associated with either an X-ray opaque object or a region of interest (ROI). In the case of metal artifact reduction, available X-rays are those not blocked by the metal; while in the case of local reconstruction, X-rays are available if and only if they intersect the ROI. This characteristic projection mask denotes whether or not measurement is made from a source to a detector.

In step 405, to take inhomogeneousness of cone-beam data into account, a relaxation function (the discrete version of $H(\vec{x})$) is generated from the projection mask, the cone-beam imaging geometry and the scanning locus. Then, in steps 404 and 406, cone-beam projection data are estimated based on an initial image volume using a ray-tracing technique.

In step 407, discrepancies between measured and estimated projection data are computed as either the ratio (EM-like iterative deblurring) or the normalized difference (ART-like iterative deblurring) for each combination of detector and source locations. In step 408 and 407, to obtain an updated image, these discrepancies (either ratios or differences) are backprojected over a 3D image grid, multiplied (EM-like iterative deblurring) or added (ART-like iterative deblurring) with an intermediate image in step 409, which is the initial image volume for the first iteration, and divided by the relaxation factor.

In step 410, a priori knowledge, such as a known image support, can be enforced upon the updated image, and reconstruction errors may be estimated in image and/or projection domains. A decision may be made in step 411 to continue the iterations, and finally in step 412, the reconstructed image may be output to, for example, workstation 110, or any other suitable device or system, for further processing or viewing.

Figure 5:
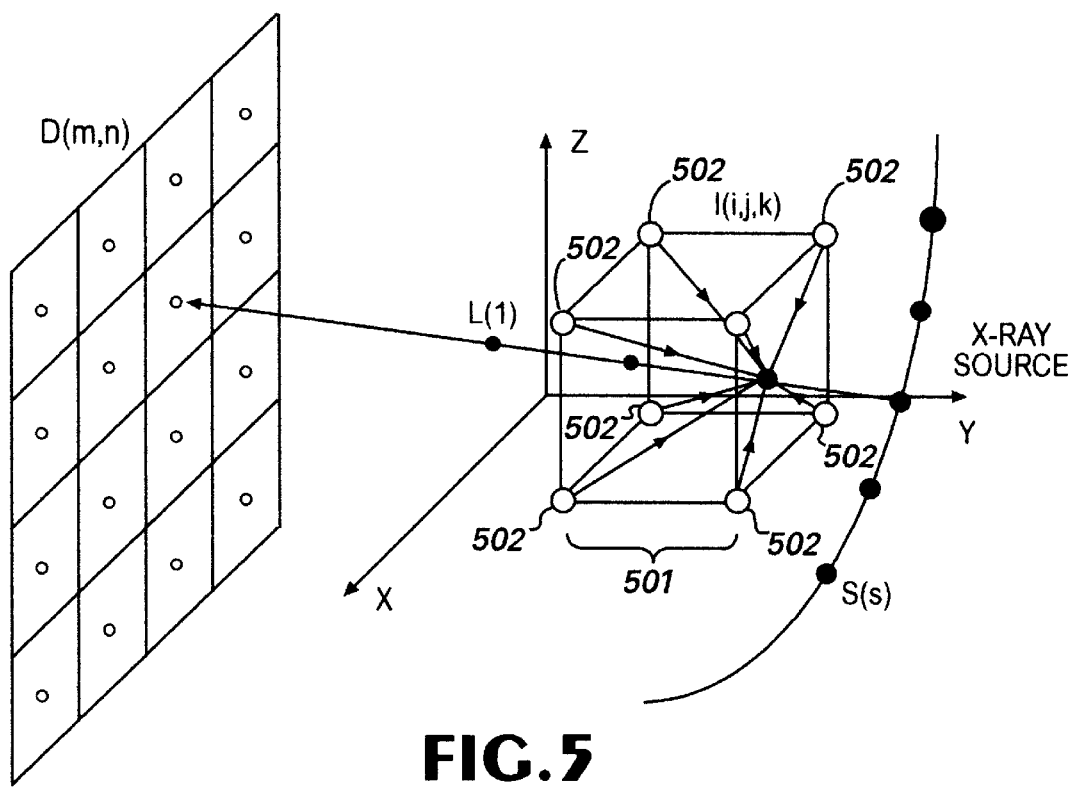
FIG. 5 illustrates the discretized reprojection process.

Additional details of the reprojection and the backprojection steps discussed above are provided below with respect to FIGS. 5 and 6. In either reprojection or backprojection, each of the X-rays is evenly divided with a pre-specified interval length (for example, the voxel side length 501), being consistent to the above discrete cone-beam imaging model. In reprojection, and as shown in FIG. 5, the voxel values of eight nearest neighbors 502 of each dividing point contribute to the projection value via bi-linear interpolation.

Figure 6:
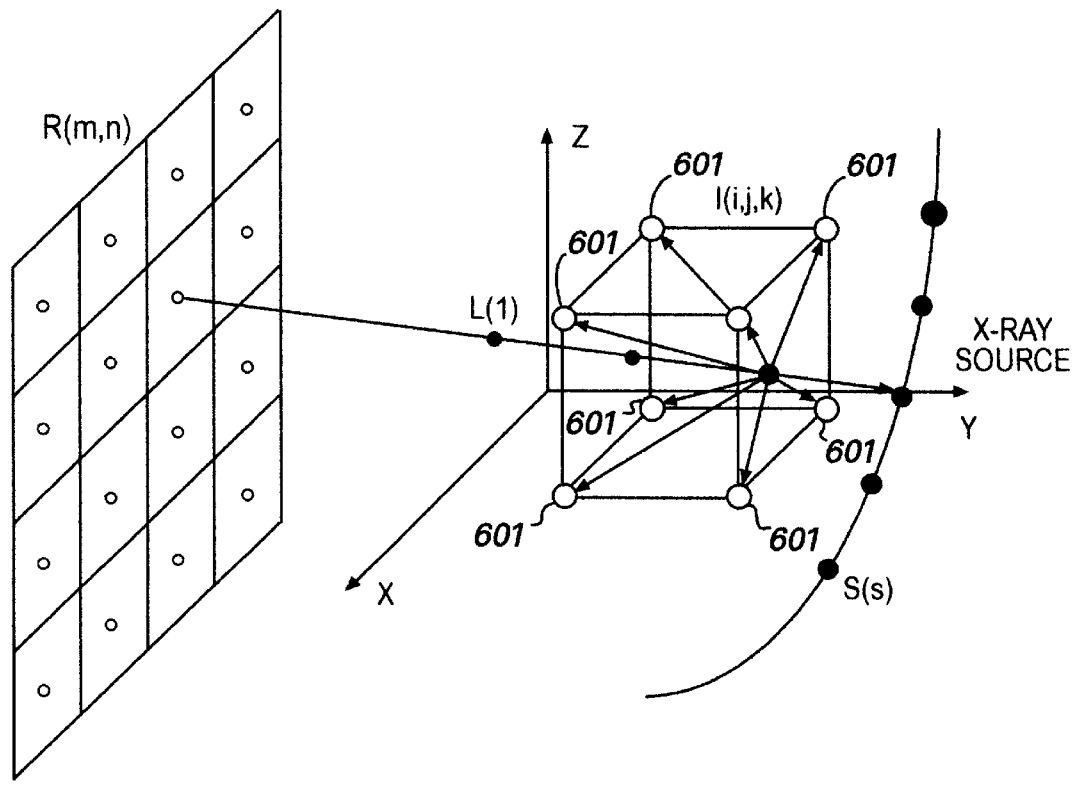
FIG. 6 illustrates the discretized backprojection process.

In backprojection, and as shown in FIG. 6, a projection value is additively re-distributed to the eight nearest neighbors 601 of each dividing point after weighting with corresponding bi-linear interpolation coefficients. Note that reprojection and backprojection can also be computed in other ways with different efficiencies and accuracies.

The iterative cone-beam process of FIG. 4 may be readily implemented in parallel processing hardware because of the parallel nature of the computational structure. That is, the processor 101 of FIG. 1 may be any parallel processing computer system, as is known in the art.

Figure 7:
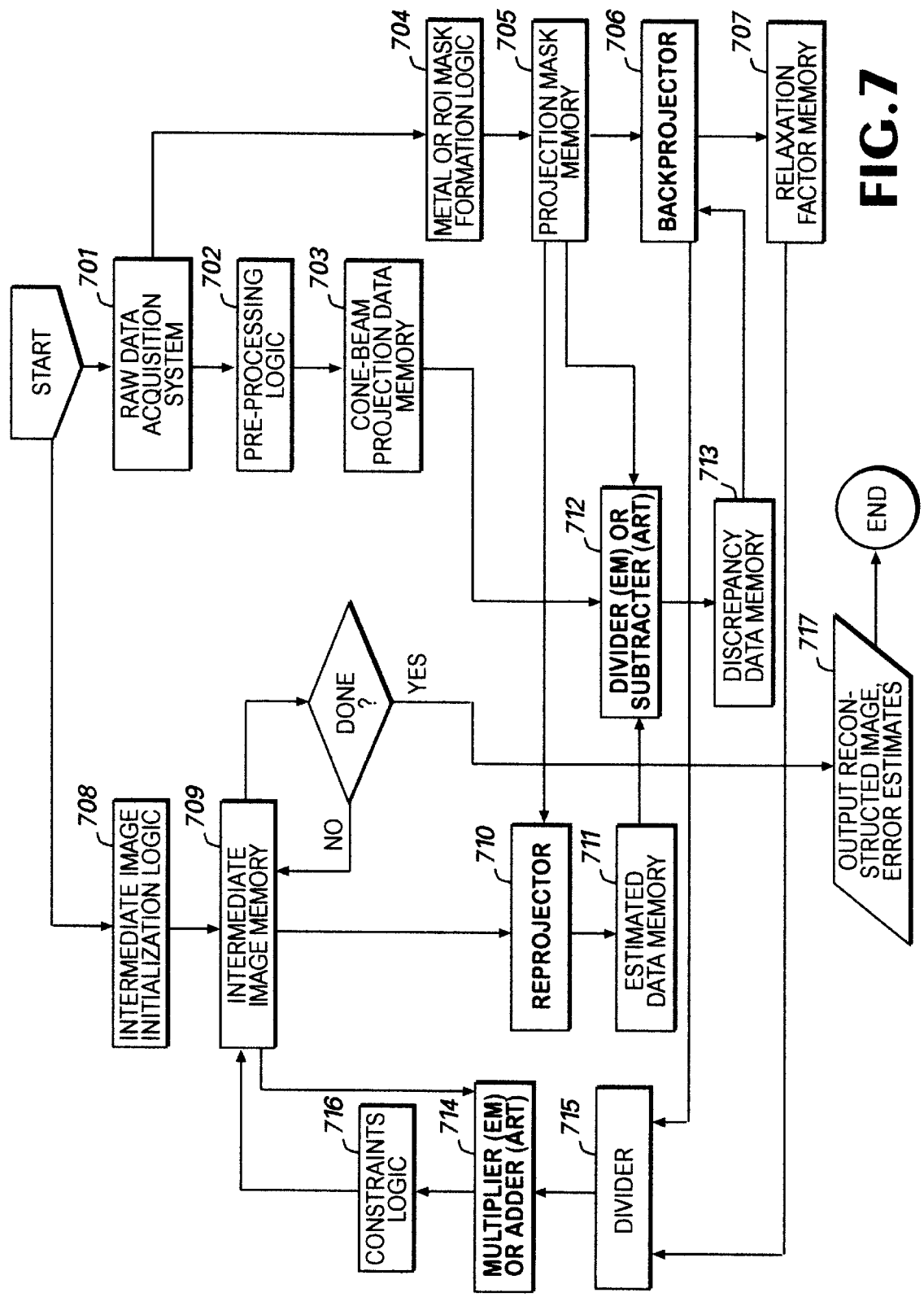
FIG. 7 is a block and process diagram depicting the EM-like and ART-like iterative cone-beam reconstruction process.

An overall process that may be performed by a parallel (or serial) processor that implements the iterative system of the present invention is shown in FIG. 7. In step 701, the raw data is first acquired. In step 702, cone-beam measures are first processed and calibrated with reference signals by a preprocessing logic to convert the measures into cone-beam projection data (ray-sums). These cone-beam data may thereafter be stored in step 703 in an allocated memory space within processor 110 (or in any other suitable storage location).

Based on measured cone-beam data, a characteristic projection mask is formed in step 704 to indicate whether or not a reading is significant for a combination of source and detector positions. A reading of a detector is discarded if the photon count is zero or too low. If there are X-ray opaque structures in an object, few photons will be detected by some detectors, and corresponding data lost. If the cone-beam aperture is not sufficiently large, not all of the source and detector positions needed for exact reconstruction are available. All these types of data incompleteness are summaried in the projection mask stored in step 705.

The projection mask stored in step 705 is critical in generating a relaxation factor, which is computed via back-projection (step 706) and saved in a relaxation factor memory space (step 707). The backprojection operation may be performed in a parallel or serial fashion by a backprojector (step 706), which is a hardware version of the backprojection computation described previously.

To start the iterative reconstruction, an initial image volume in an intermediate image memory space is needed. The intermediate image stored in memory in step 709 is initialized by an intermediate image initialization logic in step 708. Then, the intermediate image is fed into a reprojector (step 710), which may simulate the physical cone-beam projection process in hardware based on the intermediate image. The estimated projection data are saved in the estimated data memory space in step 711, which again may be within processor 110 or elsewhere.

Real cone-beam data and estimated data are point-wise compared (divided by a divider in the EM-like iterative reconstruction, or subtracted by a subtractor in the ART-like iterative reconstruction) in step 712 to produce discrepancies of measured and estimated projection data, and put in a discrepancy data memory region in step 713. The discrepancies are backprojected over the image reconstruction grid by the backprojector 706 to produce a backprojected image. The backprojected image is then voxel-wise divided by the relaxation factor in step 715, which is then multiplied or added in step 714 by the intermediate image voxel-wise to update the intermediate image.

Various constraints can be enforced upon the updated image in step 716. After updating the intermediate image, the refinement steps can be repeated until the reconstruction is satisfactory. Note that the projection mask in step 705 controls both the reprojector (step 710) and the backprojector (step 706) in the iteration so that the computations are significant.

The result of the above-described steps (701–716) is a reconstructed image in step 717.

2. Numerical Simulation

To demonstrate the feasibility of the iterative processes of the present invention for cone-beam reconstruction from incomplete data, iterative processes according to the teachings of the present invention may be coded in C on a SGI $O_2$ workstation, available from Silicon Graphics, Inc. of Mountain View, Calif., USA, using numerical simulation done with synthetic noise-free and noisy projection data based on several mathematical phantoms.

In the computer implementation of the iterative processes, the primary operations are reprojection and backprojection. As mentioned previously, because image and projection data are available only on 3D and 2D grids respectively, bi-linear interpolation may be performed to compute a projection value along a ray as well as backprojection contributions from various orientations. Of course, other methods are possible.

In formation of the projection mask, every possible synthetic projection value may, for purposes of numerical simulation, be compared to a threshold of 0.0001 HU, and whether or not the associated X-ray intersected the mask decided. The projection mask may then be backprojected over the field of view to compute the relaxation function (the discrete version of $H(\vec{x})$). The initial image volume may be arbitrarily set to 20 HU. The constraint of the known support may be enforced in all backprojection operations by keeping zero values at the grid points outside the support.

In the simulation, images may be 64 by 64 by 64 matrices. A point X-ray source and point detectors may be assumed. A planar detection array may have 64 by 64 detectors, and may be placed through the vertical axis of the reconstruction coordinate system and toward the X-ray source.

The source-to-origin distance may be 40 mm. Circular scanning and 40 projections with and without additive noise may be used. Three noise generators may be implemented according to the rejection method, which produce uniform, Gaussian and Poisson noises, respectively.

A. Test One: Disk Phantom

The first test was performed with a disk phantom that consists of a cylinder of 100 Hounsfield unit (HU), radius 10 mm and height 20 mm, and seven disks of 500 HU, radius 8 mm and height 1 mm that were horizontally oriented with their isocenters distributed on a vertical axis and 2 mm apart evenly. The background outside the phantom was set to zero.

A 3D reconstruction coordinate system was associated with the phantom in a natural manner. To evaluate the effectiveness of our iterative algorithms for metal artifact reduction, a metallic sphere of radius 4 mm was embedded in the phantom with its center at (2, 2, 2) in unit of mm. In the case of local reconstruction, the ROI was specified as a cylinder of radius 6 mm and height 16 mm, embedded in the cylindrical phantom symmetrically.

Figure 8:
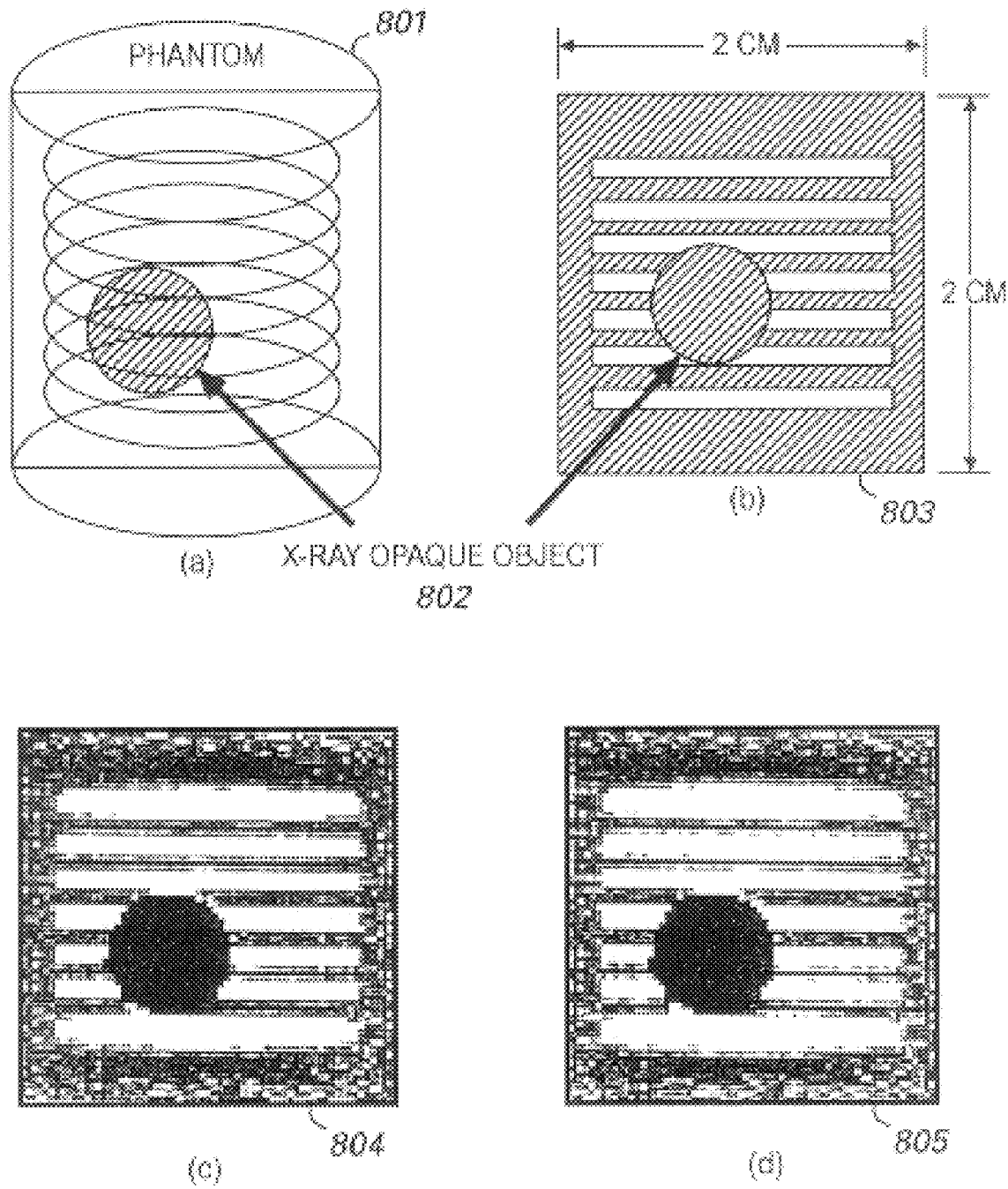
FIGS. 8A–8D depict in various stages the reconstruction of a disk phantom from incomplete data.

Representative images are depicted in FIGS. 8A–8D and 9A–9D in the case of cone-beam projection data with additive homogeneous noise in [0, 45] HU. 40 iterations were performed. FIGS. 8A–8D illustrates the iteratively reconstructed phantom 801 from incomplete data due to the embedded metallic sphere 802, where FIG. 8A shows a diagram of the phantom 801 (disk thickness not shown) and the metallic sphere 802. FIG. 8B depicts the middle sagittal slice 803, FIG. 8C depicts the counterpart 804 reconstructed via EM-like iterative deblurring, and FIG. 8D depicts the counterpart 805 via ART-like iterative deblurring.

Figure 9:
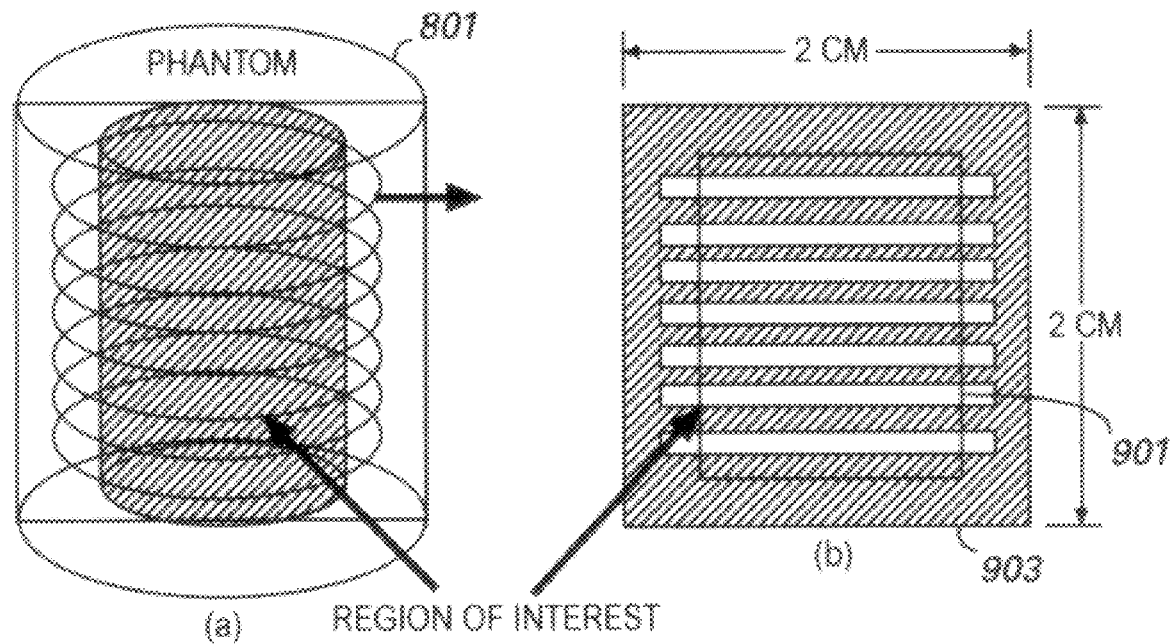
FIGS. 9A–9D depict in various stages the reconstruction of a disk phantom from truncated data.
Figure 9:
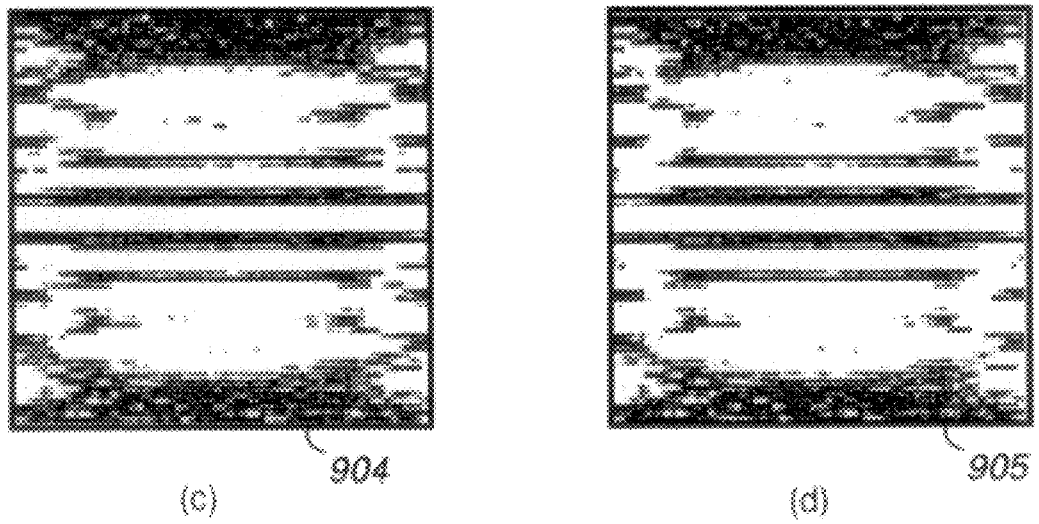

FIGS. 9A–9D illustrate the reconstructed phantom 801 from truncated data collected only with those cone-beam X-rays that intersected the ROI 901, where FIG. 9A depicts the ROI 901, FIG. 9B depicts the middle sagittal slice 903, FIG. 9C depicts the counterpart 904 reconstructed via the EM-like iterative deblurring, and FIG. 9D depicts the counterpart 905 via the ART-like iterative deblurring.

Clearly, the major structures of the phantom 801 were satisfactorily resolved without significant image noise although the data were incomplete and noisy. Also, substantial longitudinal blurring can be observed in the reconstructed images, which can be explained by the incompleteness of the circular scanning locus. There is a fundamental reason for the fact that the reconstruction bias in terms of HU was less for metal artifact reduction (FIGS. 8C and 8D) than for local reconstruction (FIGS. 9C and 9D); that is, metal artifact reduction is uniquely solvable, while local reconstruction is not.

Figure 10:
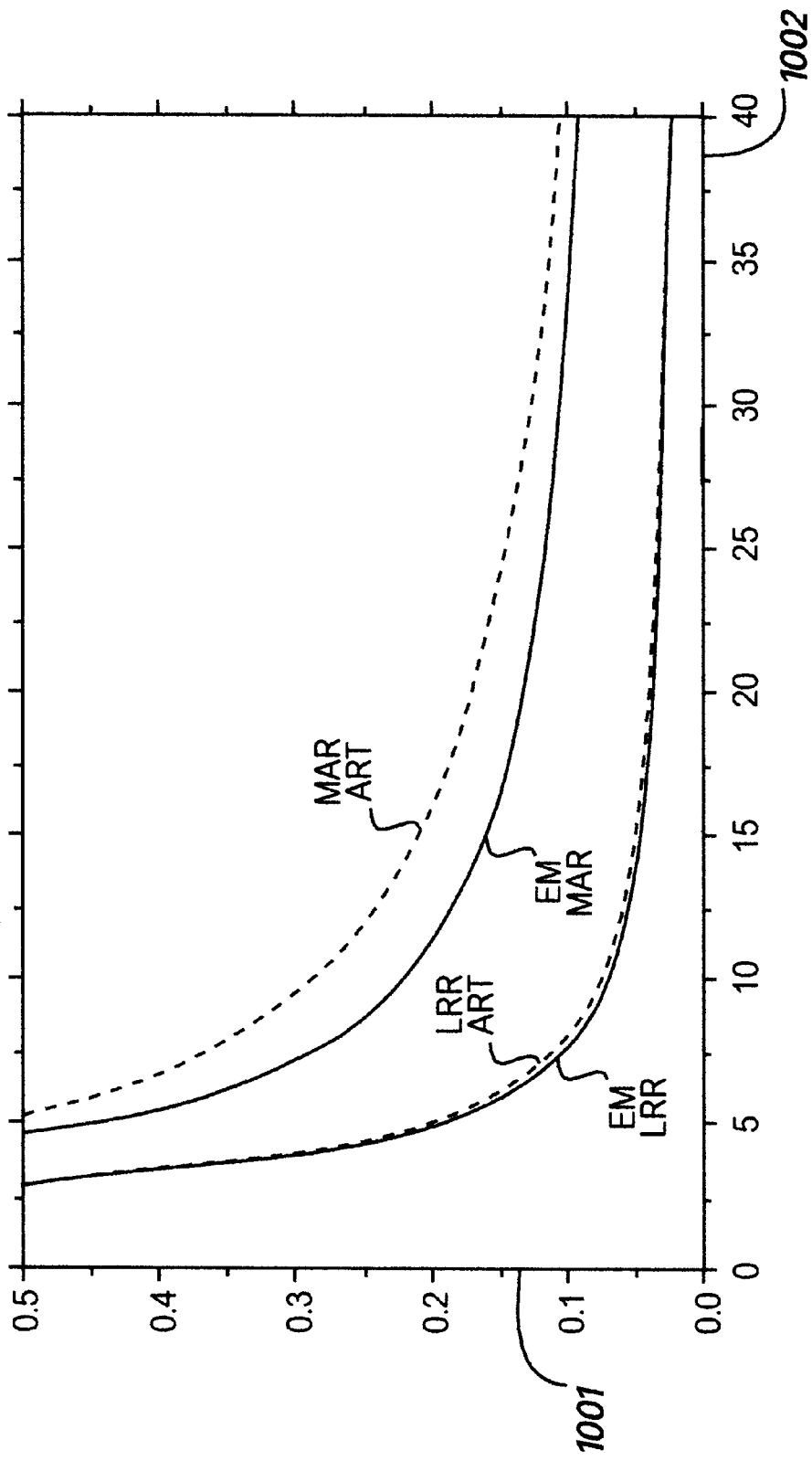
FIG. 10 is a chart illustrating I-divergence with respect to the iteration number in EM-like and ART-like iterative cone-beam tomography for metal artifact reduction and local region reconstruction.

FIG. 10 plots I-divergence (axis 1001) with respect to the iteration number (axis 1002) in EM-like and ART-like iterative cone-beam tomography for metal artifact reduction (MAR) and local region reconstruction (LRR), as shown in FIGS. 8A–8D and 9A–9D. The iteration was stopped when the discrepancy curve became relatively flat, which was subjectively selected to be 40 in this test. After this point, although more iterations would further reduce the discrepancies, the gain would be less, and image noise and artifacts stronger.

Figure 11:
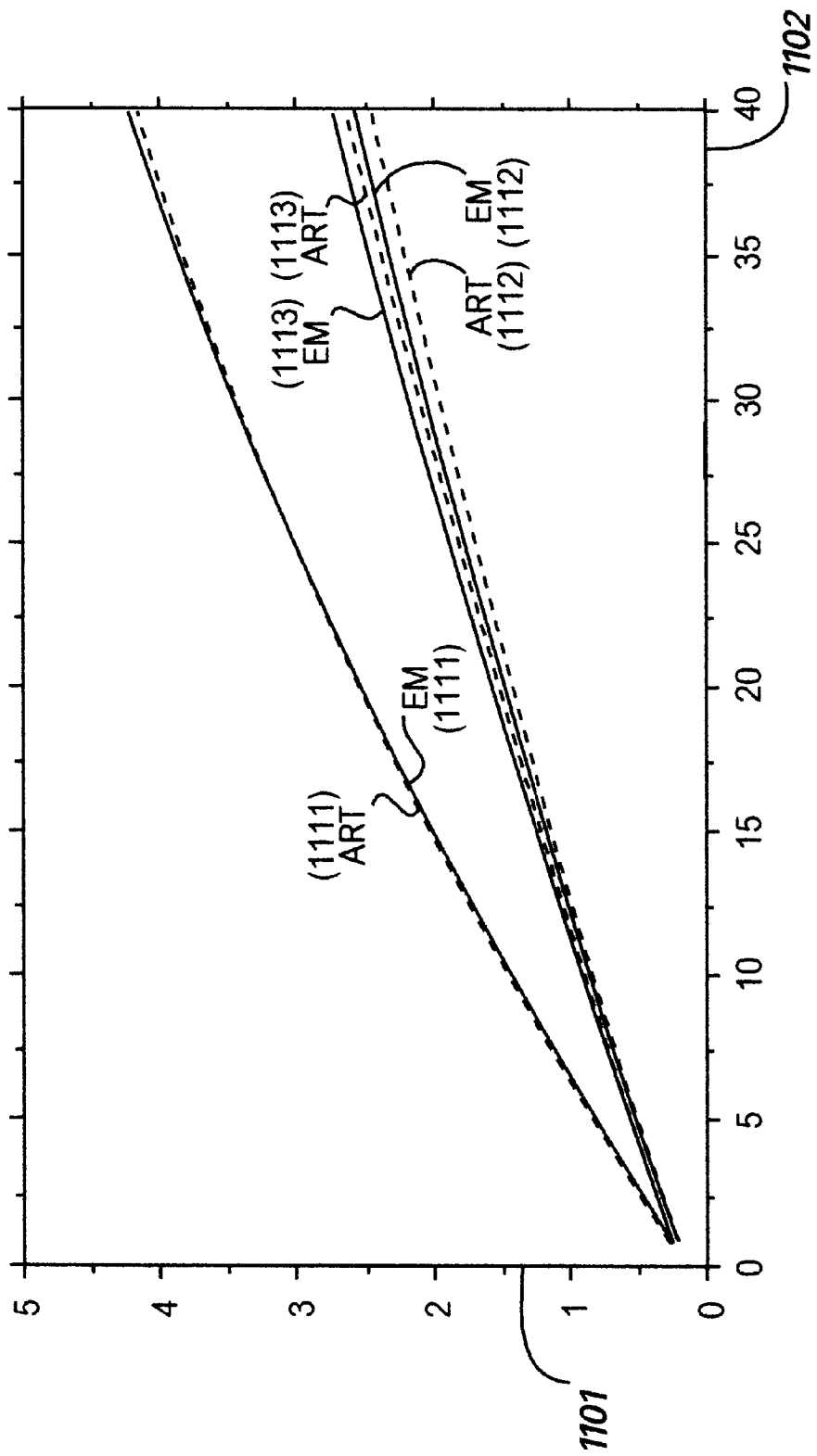
FIG. 11 is a chart illustrating image noise standard deviation with respect to the iteration number in EM-like and ART-like iterative cone-beam reconstruction of a synthesized water phantom.

The disk phantom was then transformed into a "water" phantom by taking the high-density disks away and setting the background to 20 HU. The image noise measured in a cylindrical ROI of height 2 mm and radius 5 mm, which is vertically centered in the phantom. FIG. 11 depicts image noise standard deviation (axis 1101) with respect to the iteration number (axis 1102) in EM-like and ART-like iterative cone-beam reconstruction of the water phantom for projection data with additive uniform (1111), Gaussian (1112) and Poisson (1113) noises, respectively. The standard deviations of these three types of noise were 2.6, 3.0 and 3.0 respectively, all in HU. The increasing trend indicates the need for regularization, a fact that is well known in the field.

B. Test Two: Dental Phantom

A three-dimensional dental phantom was designed that consists of two parts: (1) a 200 HU background cylinder of radius 10 cm and height 20 cm, modeling the soft tissue; and (2) a 1000 HU semi-cylinder of height 10 cm, inner and outer radii 7 cm and 8 cm respectively, representing the dental arch and teeth. A metallic dental restoration (e.g., tooth filling) was assumed to be an opaque cylinder of radius 1 cm and height 4 cm, and vertically centered at (5.3, 5.3) in-plane in unit of cm with equi-distances from the top and bottom surface of the phantom. The initial guess was arbitrarily selected to be 20 HU.

Figure 12:
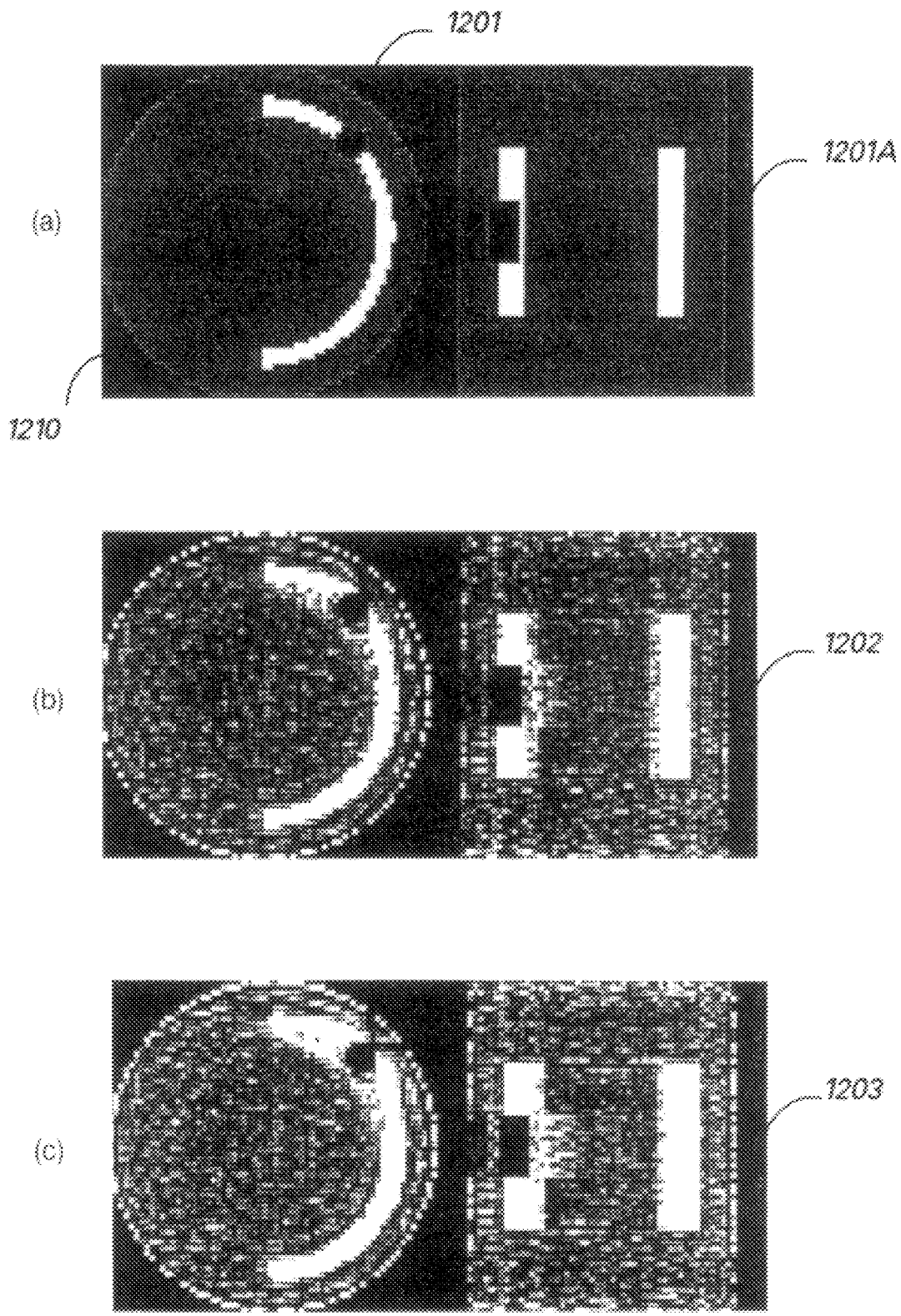
FIGS. 12a–12c depict in various stages a reconstructed dental phantom from incomplete data due to an embedded metallic cylinder.

FIGS. 12A–12C show reconstruction simulation via the EM-like and ART-like algorithms using projection data with Gaussian noise after 80 iterations. FIG. 12A depicts representative transaxial and sagittal slices 1201, 1201A of the phantom 1210, FIGS. 12B and 12C depict the corresponding images 1202 and 1203 reconstructed respectively through EM-like and ART-like iterative deblurring from projection data with additive Gaussian noise of standard deviation 30 HU.

Figure 13:
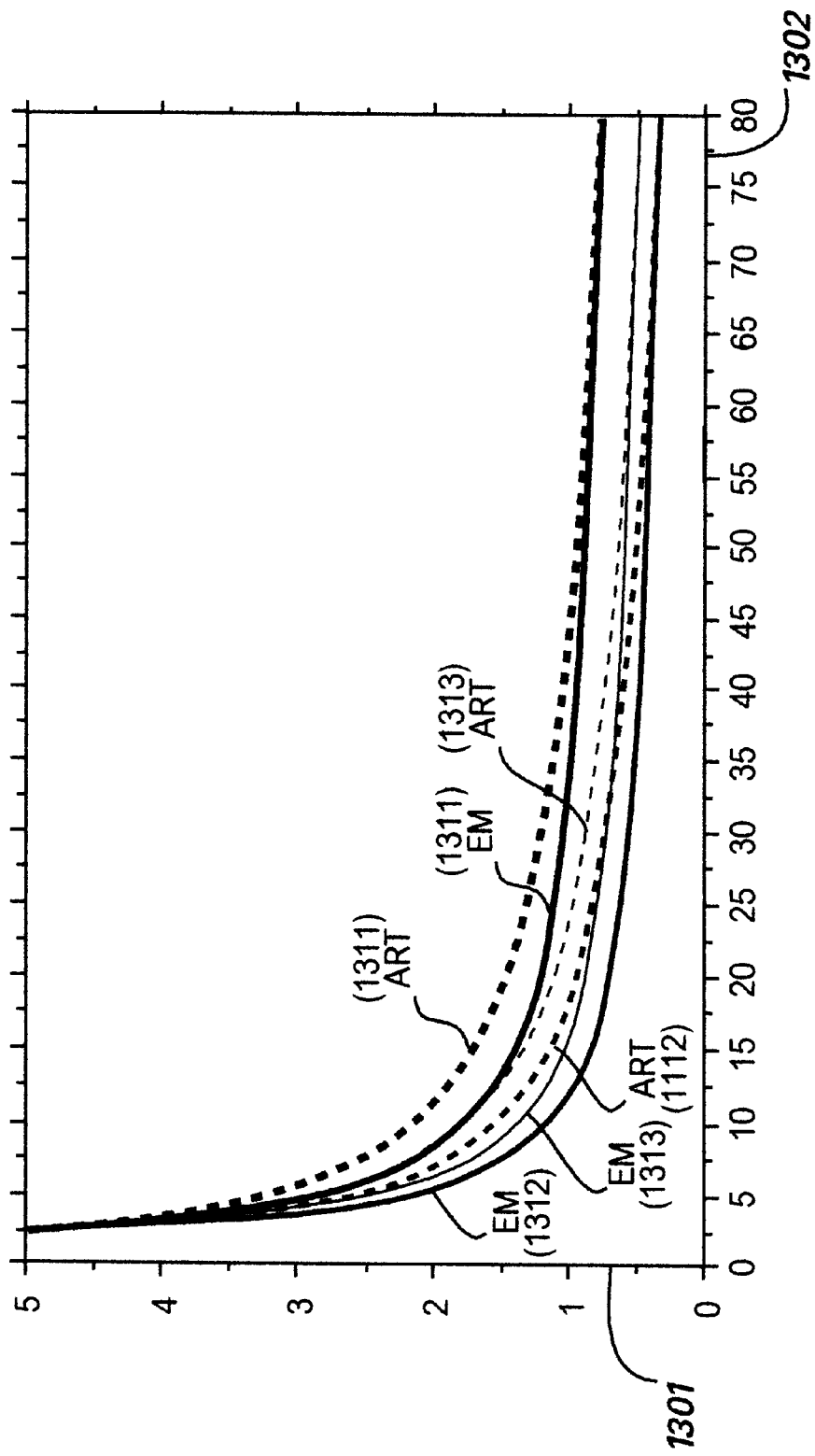
FIG. 13 is a chart illustrating I-divergence with respect to the iterative number in EM-like and ART-like iterative cone-beam metal artifiact reduction.

FIG. 13 illustrates I-divergence (axis 1301) as a function of the iteration number (axis 1302) in EM-like and ART-like iterative cone-beam reconstruction of the dental phantom. In this case for the projection data with additive uniform (1311), Gaussian (1312) and Poisson (1313) noises, their standard deviations were ten times larger than what were used in the previously described water phantom test. The image noise was also measured in a centralized cylindrical ROI.

Given the nature of the simulations performed above, it is difficult to make a thorough comparison between EM- and ART-like iterative algorithms. However, through experimentation, it has been found that the EM-like and ART-like processes performed similarly in terms of visual inspection, image noise, I-divergence between measured and reprojected data.

C. Test Three: Realistic Phantom

Although direct testing using real scans is difficult to perform because manufacturers of CT scanners consider raw data formats proprietary, a more realistic phantom was created from an actual infant head CT image. The phantom was a 64 by 64 by 50 image volume. An ellipsoidal metal part was then placed in the head for EM-like and ART-like reconstruction using the same parameters as used in Tests 1 and 2 described previously, except that the noise was not added.

Figure 14:
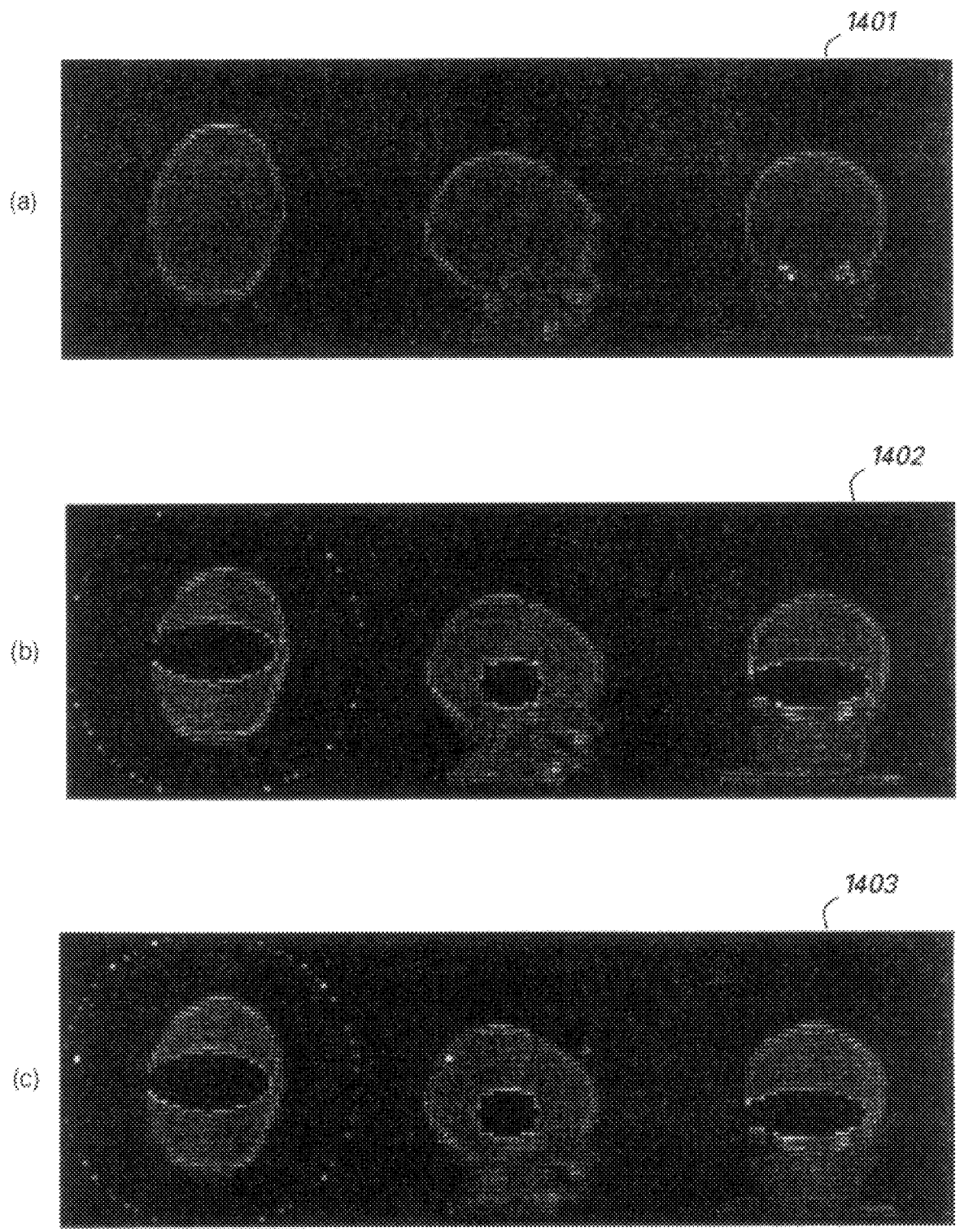
FIGS. 14a–14c depict in various stages a reconstructed head from incomplete data due to an embedded metallic ellipsoid.

FIGS. 14A–14C demonstrate the realistic simulation of EM-like and ART-like cone-beam reconstruction after 40 iterations, where FIG. 14A depicts three orthogonal sections 1401 of the infant head, FIG. 14B depicts the corresponding images 1402 reconstructed through EM-like iterative deblurring, and FIG. 14C depicts the images 1403 through ART-like deblurring.

Other experiments in addition to what has been reported above may also be performed. For example, the iterative algorithms worked well with a total hip prosthesis fitting phantom.

3. Analysis

Compared to existing X-ray cone-beam reconstruction algorithms, the EM-like iterative deblurring algorithm is unique in the two aspects. First, the EM-like algorithm is optimal in the sense of I-divergence minimization. It was previously known that the EM-like formulation can be applied for deterministic linear deblurring with a positive blurring kernel to minimize I-divergence. It has now been established that the properties of the EM-like iterative deblurring sequence essentially remain with a non-negative blurring kernel. Because X-ray CT should be considered as linear deblurring with a non-negative blurring kernel, the present invention consolidates the foundation for use of the EM-like iterative deblurring formula in deterministic transmission X-ray CT.

Second, the EM-like algorithm handles data incompleteness via introduction of the projection mask. Most importantly, a three-dimensionally varying relaxation factor is generated from the projection mask, and the EM-like algorithm iterates according to such a relaxation scheme. Traditionally, the relaxation coefficient of iterative reconstruction for metal artifact reduction is constant in each iteration, and may be adjusted with some freedom between iterations. In the present invention, the same spatially varying relaxation coefficients compensate for non-uniform densities of available cone-beam rays in every iteration.

I-divergence is asymmetric. What is minimized in the present EM-like iterative cone-beam algorithm is I-divergence between measured and estimated data. It is equally reasonable to minimize I-divergence between estimated and measured data. Others have considered this in a more general setting. For $\vec{x} > 0$ and $0 < \alpha \leq 1$, two minimization problems have been formulated by others: (1) minimize $F(\vec{x}) = \alpha I(\vec{a} \| \vec{b}) + (1-\alpha) I(\vec{p} \| \vec{c})$, and (2) minimize $G(\vec{x}) = \alpha I(\vec{b} \| \vec{a}) + (1-\alpha) I(\vec{c} \| \vec{p})$, where $\vec{p}$ is a prior estimate of $\vec{c}$. Using an alternating projection approach, a set of iterative formulas for regularized non-negative linear deblurring has been derived by others. These iterative formulas were shown to produce a unique solution in almost all cases.

It seems that these results can be similarly adapted for regularized iterative cone-beam reconstruction. Note that not all possible iterative formulas are equally good, and mean and variance of alternative formulas should be analyzed either theoretically or numerically, and the bias-variance tradeoff made.

Two comments on the ART-like iterative deblurring algorithm are provided below. First, the ART-like iterative deblurring algorithm is heuristically related to the EM-like iterative deblurring algorithm. The ART-like iterative deblurring formula is heuristically derived by quantifying the discrepancy between measured and predicted data using difference, while the EM-like iterative deblurring formula can be similarly derived by quantifying the discrepancy between measured and predicted data using ratio. Therefore, the ART-like and EM-like formulas may be regarded as additive and multiplicative deblurring methods, respectively. The ART-like iterative deblurring algorithm also leads to spatially varying relaxation as the EM-like counterpart.

Second, the convergence of the ART-like iterative deblurring formula may be studied—ART and its variants have been extensively studied over years. However, it is believed that the particular form of the ART-like iterative deblurring formula used for purposes of the present invention has not been used before. Inclusion of this additive formula is for a fair comparison between EM-like and ART-like methods, because the ART method in the classical form (spatially invariant relaxation) is clearly inferior to the ART-like iterative deblurring formula used in the present invention in metal artifact reduction. There is suggestive evidence that the ART-like iterative deblurring formula converges.

Although a deterministic interpretation has been given to the EM-like iterative deblurring formula as described with respect to the present invention, it is also possible to attach a statistical meaning to the formula. Actually, maximizing the mean value of the log-likehood is equivalent to minimizing I-divergence when quantum-limited or signal-dependent noise is present in data, as recognized by others. It is hypothesized that the additive deblurring formula might maximize likelihood when data are corrupted by Gaussian noise.

In the simulation of the present invention described previously, analytic cone-beam algorithms have been omitted, because they are not suitable when portions of data are missing. In this case, high-pass filtering would cause significant undershoots and overshoots in data, substantial distortion and artifacts in images, as shown in the prior art. However, it is interesting to note that the filtered backprojection reconstruction and the iterative cone-beam reconstruction share the same projection and backprojection processes. In each iteration for cone-beam reconstruction, projection data are computationally synthesized from an intermediate image, then ratios or differences between measured and synthesized data are backprojected to update the intermediate image. Both projection and backprojection are computationally expensive. Because computing technology evolves rapidly and the iterative algorithms are parallelizable, the potential for improvement in computational speed is clearly tremendous.

In conclusion the present invention makes use of EM-like and ART-like iterative algorithms for X-ray cone-beam tomography from incomplete data and noisy data. The feasibility of the present invention has been demonstrated in numerical simulation of metal artifact reduction and local reconstruction.

Although the present invention has been described with particular reference to certain preferred embodiments thereof, variations and modifications of the present invention can be effected within the spirit and scope of the following claims.

What is claimed is:

1. A process for reconstructing an image from a cone-beam tomographic system, wherein each frame of the image has an associated cone-beam geometry, and wherein the tomographic system has various geometries and scanning loci, the process comprising the steps of:

(a) receiving measured projection data from a cone-beam tomographic system;

(b) generating a projection mask associated with the measured projection data;

(c) generating a relaxation function from the projection mask, the tomographic system geometry and the scanning locus;

(d) generating an intermediate image corresponding to an initial image volume associated with the imaging geometry;

(e) estimating the projection data based upon the intermediate image;

(f) calculating discrepancies between the measured projection data and the estimated projection data;

(g) backprojecting the discrepancies over a 3D image grid;

(h) combining the backprojected discrepancies with the intermediate image, thereby updating the intermediate reconstructed tomographic image;

(i) repeating steps (e)–(h) until the intermediate reconstructed tomographic image coverges, and (j) outputting the reconstructed tomographic image.

2. The process of claim 1, wherein the outputting step comprises the sub-step of displaying the reconstructed tomographic image on a video display.

3. The process of claim 1, wherein the combining step is performed according to an EM-like iterative deblurring process.

4. The process of claim 1, wherein the combining step is performed according to an ART-like iterative deblurring process.

5. A process for reconstructing an image from a cone-beam tomographic system, wherein each frame of the image has an associated cone-beam geometry, and wherein the tomographic system has various geometries and scanning loci, the process comprising the steps of:

(a) receiving measured projection data from a cone-beam tomographic system;

(b) generating a projection mask associated with the measured projection data;

(c) generating a relaxation function from the projection mask, the tomographic system geometry and the scanning locus;

(d) generating an intermediate image corresponding to an initial image volume associated with the imaging geometry;

(e) estimating the projection data based upon the intermediate image;

(f) calculating discrepancies between the measured projection data and the estimated projection data;

(g) backprojecting the discrepancies over a 3D image grid;

(h) combining the backprojected discrepancies with the intermediate image, thereby updating the intermediate reconstructed tomographic image;

(i) repeating steps (e)–(h) a selected number of times, and (j) outputting the reconstructed tomographic image.

6. A system for reconstructing a cone-beam tomographic image, comprising:

(a) a cone-beam tomographic means for generating measured projection data, wherein the cone-beam tomographic means has an associated geometry and scanning locus; and (b) a data and image processing means for performing the steps of:

(i) receiving the measured projection data from the cone-beam tomographic means;

(ii) generating a projection mask associated with the measured projection data;

(iii) generating a relaxation function from the projection mask, the cone-beam tomographic means geometry and the scanning locus;

(iv) generating an intermediate image corresponding to an initial image volume associated with the imaging geometry;

(v) estimating the projection data based upon the intermediate image;

(vi) calculating discrepancies between the measured projection data and the estimated projection data;

(vii) backprojecting the discrepancies over a 3D image grid and scaling the backprojected result with the relaxation factor;

(viii) combining the backprojected discrepancies with the intermediate image to update the intermediate image;

(ix) repeating the steps (v)–(viii) until the image quality is satisfactory.

7. The system of claim 6, wherein the combining step is performed according to an EM-like iterative deblurring process.

8. The system of claim 6, wherein the combining step is performed according to an ART-like iterative deblurring process.

9. The system of claim 6, wherein the cone-beam tomographic means comprises an industrial cone-beam imaging system.

10. The system of claim 6, further comprising an imaging system means for receiving the reconstructed tomographic image and displaying it to a user of the imaging system.

11. The system of claim 10, wherein the imaging system means comprises a high-performance graphical workstation.

12. A system for reconstructing a cone-beam tomographic image, comprising:

(a) a cone-beam tomographic means for generating measured projection data, wherein the cone-beam tomographic means has an associated geometry and scanning locus; and (b) a data and image processing means for performing the steps of:

(i) receiving the measured projection data from the cone-beam tomographic means;

(ii) generating a projection mask associated with the measured projection data;

(iii) generating a relaxation function from the projection mask, the cone-beam tomographic means geometry and the scanning locus;

(iv) generating an intermediate image corresponding to an initial image volume associated with the imaging geometry;

(v) estimating the projection data based upon the intermediate image;

(vi) calculating discrepancies between the measured projection data and the estimated projection data;

(vii) backprojecting the discrepancies over a 3D image grid and scaling the backprojected result with the relaxation factor;

(viii) combining the backprojected discrepancies with the intermediate image to update the intermediate image;

(ix) repeating the steps (v)–(viii) a selected number of times.

* * * * *

UNITED STATES PATENT AND TRADEMARK OFFICE
CERTIFICATE OF CORRECTION

PATENT NO. : 5,909,476

DATED : 6/1/99

INVENTOR(S) : Cheng et al.

It is certified that error appears in the above-identified patent and that said Letters Patent is hereby corrected as shown below:

Column 1, line 4, please insert the following:

This invention was made with government support under NIDDK R29 DK50184; NINDS R01 NS35368; and 1 R03 DC 02798-01 awarded by the National Institutes of Health. The government has certain rights in the invention.--

Signed and Sealed this

Eleventh Day of January, 2000

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO.   : 5,909,476                                    Page 1 of 1
DATED        : June 1, 1999
INVENTOR(S)  : Cheng et al.

It is certified that error appears in the above-identified patent and that said Letters Patent is hereby corrected as shown below:

Please list the inventors in the following order as originally filed:
INVENTOR(S):    Ge Wang, Donald L. Snyder, Joseph A. O'Sullivan, Ping-Chin Cheng, and Michael W. Vannier <u>Title page,</u>
Under Item [19], "Cheng et al." should be-- Wang et al. --.

Signed and Sealed this

Second Day of October, 2001

Attest:

*Nicholas P. Godici*

NICHOLAS P. GODICI
*Attesting Officer*    *Acting Director of the United States Patent and Trademark Office*